United States Patent [19]

Damon, II

[11] 4,420,475

[45] Dec. 13, 1983

[54] SILICON-BEARING AMIDES

[75] Inventor: Robert E. Damon, II, Randolph, N.J.

[73] Assignee: Sandoz, Inc., E. Hanover, N.J.

[21] Appl. No.: 215,414

[22] Filed: Dec. 11, 1980

Related U.S. Application Data

[63] Continuation-in-part of Ser. No. 80,424, Oct. 1, 1979, abandoned, which is a continuation-in-part of Ser. No. 74,002, Sep. 10, 1979, abandoned.

[51] Int. Cl.³ .................... C07F 7/10; A01N 55/00; A61K 31/695
[52] U.S. Cl. .................... 424/184; 556/419; 260/404; 548/406
[58] Field of Search ....... 556/419; 260/404, 326.13 R, 260/326.13 A, 326.13 B, 326.13 C, 326.13 D; 424/184; 548/406

[56] References Cited

U.S. PATENT DOCUMENTS

| | | | |
|---|---|---|---|
| 2,607,793 | 8/1952 | Sommer | 556/419 |
| 2,610,198 | 9/1952 | Sommer | 556/419 |
| 2,919,173 | 12/1959 | Roff | 556/419 X |
| 2,973,383 | 2/1961 | Black | 556/419 UX |
| 4,088,668 | 5/1978 | Metcalf et al. | 556/419 X |
| 4,297,349 | 10/1981 | Barcza | 556/419 X |
| 4,328,216 | 5/1982 | Toyoshima et al. | 556/419 X |

OTHER PUBLICATIONS

"(Alkoxyethynyl) Silanes" by R. I. Pal'chik et al., translated from Zhurnal Obschei Khimii, vol. 39, No. 8, pp. 1792-1796 (1969).

"Synthesis and Reactions of Trimethylsilylketene and the Tautomeric Trimethylsiloxyacetylene" by L. L. Shchukovskaya et al., translated from Doklady Akdemii Nauk SSSR, vol. 164 No. 2, pp. 357-360 (1965).

Primary Examiner—Paul F. Shaver
Attorney, Agent, or Firm—Gerald D. Sharkin; Richard E. Vila; Frederick H. Weinfeldt

[57] ABSTRACT

Compounds of the formula I:

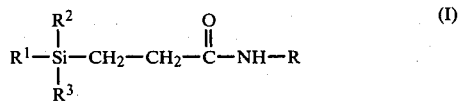

wherein each of $R^1$, $R^2$ and $R^3$ is, independently,
(a) alkyl having from 1 to 22 carbon atoms; or
(b) of the formula

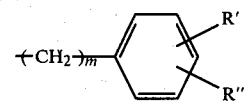

in which m is 0, 1 or 2, and each R' and R" is independently a hydrogen atom, alkyl having from 1 to 3 carbon atoms, alkoxy having from 1 to 3 carbon atoms, or halo having an atomic weight of from about 19 to 127; and R is of an aralkyl-, phenyltryptophanyl- or benzo-cycloalkyl-type, are obtained by hydrogenating corresponding α-β ethylenically-unsaturated analogs (II), which in turn are obtained by hydrogenating corresponding α-β acetylenically-unsaturated analogs. Compounds I and II are useful as anti-atheroslerotic agents.

32 Claims, No Drawings

SILICON-BEARING AMIDES

This is a continuation-in-part of copending application Ser. No. 80,424 (filed Oct. 1, 1979) which in turn is a continuation-in-part of copending application Ser. No. 74,002 (filed Sept. 10, 1979 both now abandoned).

This invention relates to silicon-bearing amides, and more particularly to a method of preparing a class of silicon-bearing amides, a subclass thereof which is novel, novel intermediates in preparation of said class of amides, and the pharmaceutical use of said novel compounds and certain intermediates, as well as pharmaceutical compositions comprising said pharmaceutically useful novel compounds and intermediates.

The final compounds (I) which are obtainable by the process of this invention may conveniently be represented by the formula I:

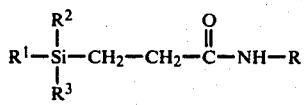
I wherein each of $R^1$, $R^2$ and $R^3$ is, independently,
(a) alkyl having from 1 to 22 carbon atoms; or
(b) of the formula

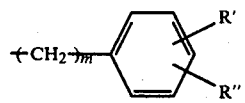

in which
m is 0, 1 or 2, and each of R' and R" is independently a hydrogen atom, alkyl having from 1 to 3 carbon atoms, alkoxy having from 1 to 3 carbon atoms, or halo having an atomic weight of from about 19 to 127; and R is of type (a) an aralkyl-type radical of the structure (a)

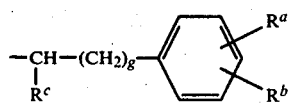

wherein
g is 0, 1 or 2;
$R^a$ is a hydrogen atom, halo having an atomic weight of from about 19 to 127, alkoxy having from 1 to 4 carbon atoms, or alkyl having from 1 to 4 carbon atoms, or trifluoromethyl;
$R^b$ is a hydrogen atom, alkyl having from 1 to 3 carbon atoms, alkoxy having from 1 to 3 carbon atoms, or halo having an atomic weight of from about 19 to 36; and
$R^c$ is subtype (i) a hydrogen atom; subtype (ii) a radical of the structure
(ii)

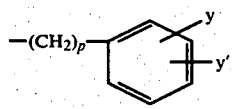

in which
p is 0, 1 or 2, and
y is a hydrogen atom, halo having an atomic weight of from about 19 to 127, alkoxy having from 1 to 4 carbon atoms, or alkyl having from 1 to 4 carbon atoms; and
y' is a hydrogen atom, alkoxy having from to 3 carbon atoms, alkyl having from 1 to 3 carbon atoms, or halo having an atomic weight of from about 9 to 36; or subtype (iii) alkyl having from 1 to 8 carbon atoms; or R is of type (b) a phenyl-type radical of the structure (b)

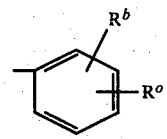

in which
$R^b$ is as defined above, and
$R^o$ is a hydrogen atom, halo having an atomic weight of from about 19 to 127, alkoxy having from 1 to 4 carbon atoms, or alkyl having from 1 to 4 carbon atoms; or
$R^o$ is a radical of the structure $R^f$:

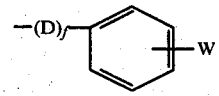

in which
D is —$CH_2$— or —O—;
f is 0 or 1; and
W is a hydrogen atom, halo having an atomic weight of from about 19 to 80, alkoxy having from 1 to 3 carbon atoms, or alkyl having from 1 to 3 carbon atoms; or R is of type (c) an indolyl radical of the structure:

(c)

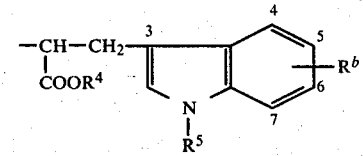

wherein
$R^b$ is as defined above;
$R^4$ is hydrogen; an equivalent of a cation which results in the formation of a salt which is pharmaceutically acceptable; alkyl having from 1 to 8 carbon atoms; or benzyl;
$R^5$ is a hydrogen atom, alkyl having from 1 to 8 carbon atoms or benzyl; or
R is (d) a benzocycloalkyl nucleus of the structure:
(d)

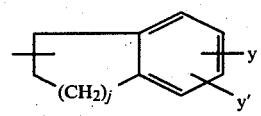

wherein
y and y' are as defined above; and
j is a whole integer of from 1 to 4.

In the above-presented definition of Compounds I, halo having an atomic weight of from about 19 to 36, includes fluoro and chloro; halo having an atomic weight of from about 19 to 80 includes fluoro, chloro and bromo; while halo having an atomic weight of from about 19 to 127 includes fluoro, chloro, bromo and iodo. Exemplary of alkyl or alkoxy having from 1 to 3 or 1 to 4 carbon atoms is methyl, or methoxy and ethoxy. Unless otherwise indicated, alkyl and alkoxy may be branched or unbranched.

Compounds I'', i.e. compounds I as defined above in which at least one of $R^1$, $R^2$ and $R^3$ is of type (b), are novel and constitute an embodiment of this invention. Those Compounds I which are not part of this invention are intended to be excluded by the above-presented proviso, although their preparation by the processes described herein constitute embodiments of this invention. Those compounds I which are excluded are described and claimed in pending application of Sandor Barcza, Serial No. 199,982 filed Oct. 23, 1980.

Particular embodiments of this invention are Compounds I (including Compounds I'') and intermediates thereof in which not more than two of $R^1$, $R^2$ and $R^3$ are of type (b). Additional sub-classes are those compounds in which two of $R^1$, $R^2$ and $R^3$ are the same, and those in which $R^2$ and $R^3$ ar alkyl, having from 1 to 3 carbon atoms, e.g. methyl, and $R^1$ is alkyl having from 8 to 14 carbon atoms, e.g. n-decyl. Preferred compounds I' are those in which $R^1=R^2=$type (b) in which m=0 or 1, particularly 0, and $R^3=$type (a). Preferred compounds I are also those in which R is of type (a); particularly where R is 1-phenyl 2-(p-tolyl)-ethyl.

Further preferred forms of Compounds I when R is of type (a) or (b) and R° is not R$^f$, are that it is preferred that when R$^a$, R° or y is other than a hydrogen atom and R$^b$ (or y') is a hydrogen atom, that R°, or R$^a$, or y be located at the 4-position; and that when R$^b$ (or y') is also other than a hydrogen atom that R$^a$ or R° and R$^b$ (or y and y') are the same, and it is additionally preferred that they be located at the 2- and 4-positions of the phenyl ring. When R is of type (a) where g=1, and R$^c$ is of type (ii) where p=0, then R can be an 1-(phenyl)-2-(p-methylphenyl) ethyl radical, and when R$^c$ is of type (ii) where p=1, then R can be an 1-(benzyl)-2 (phenyl)ethyl radical.

With particular respect to the substituent R° when it is a radical R$^f$, it will be appreciated that when D=CH$_2$ and f=1, then the radical R$^f$ is of the benzyl type. When D=oxygen and f=1, then the radical R$^f$ is of the phenoxy-type. When f=zero, then the radical R$^f$ is of the phenyl-type. Hence, when R is of type (b) and R° is of type R$^f$ where f=zero, then R can be a biphenylyl radical. The radical R$^f$ is preferably at the para-position. When W is other than a hydrogen atom, it is preferably at the para-position.

With respect to R, when it is of type (c), it is preferred that when R$^b$ is other than a hydrogen atom, it be located at the 5-position of the indole nucleus. It is also preferred that when $R^4$ is alkyl, it is unbranched, particularly ethyl.

Compounds I in which R is of type (c) may be regarded as falling into one of two subclasses, ie Compounds Ic where $R^4$ is hydrogen or a cation; and Ic' where $R^4$ is alkyl or benzyl. Compounds Ic' are preferred. Compounds Ic may be prepared directly or by hydrolyzing a corresponding compound Ic'.

A generally applicable and convenient method of carrying out the hydrolysis is to treat an appropriate Compound Ic' with a dilute aqueous solution of a water-soluble alkali hydroxide, eg. sodium or potassium hydroxide (5 to 15%) at moderate temperatures eg. 20° to 100° C., preferably in the presence of a water-miscible co-solvent, such as a lower alkanol, eg ethanol. Such hydrolysis yields a compound Ic in which $R^4$ is the cation corresponding to the respective alkali metal hydroxide employed. Such compound may be recovered as such, or the reaction mixture neutralized and the free acid form of a Compound Ic (where $R^4=$H) recovered.

In those instances where a particular Compound Ic' ester is acid-labile, rather than base-labile, eg where $R^4$ is t-butyl, an analogous procedure to that described above, can be followed except using dilute hydrochloric or sulfuric acid in place of the alkali metal hydroxide, in which case a Compound Ic in free acid form, rather than the corresponding salt of the alkali metal hydroxide is obtained. As is well understood, free acid and salt forms are inter-convertable in accordance with well known techniques.

With respect to R when it is of type (d) it is preferred that when y is other than a hydrogen atom, that it be located at a carbon atom ortho to the ring junction; and that when y' is also other than a hydrogen, it is preferred that it be the same as y, and it is additionally preferred that it be in para-relationship to y'. It is additionally preferred that the amide group be linked to a carbon of the cycloalkyl moiety which is directly bonded to a ring junction carbon. It is also preferred that j be 1, ie, that the benzocycloalkyl nucleus be indanyl, and particularly 1-indanyl.

In the above-presented definitions, when R°, $R^1$ or y is halo, it is preferably fluoro or chloro, and particularly chloro; and when $R^2$ or y' is halo it is preferably chloro.

Those compounds I which are other than Ic are defined hereinafter as I'. Hereinafter, R' is the same as R, but when it is of type (c), then $R^4$ is alkyl or benzyl, ie it is other than H or a cation. Intermediates of Compounds I are compounds II and III, hereinafter described. Analogous to Compound I', those compounds II and III in which R is R' are designated as II' and III', respectively, and corresponding analogs of Ic' and Ic; are IIc' and IIc; and IIIc' and IIIc. Hence, just as I=I'+Ic; II=II'+IIc; and III=III'+IIIc.

The above-described compounds I are obtainable by reduction of corresponding ethylenically unsaturated silicon-bearing compounds of formula II:

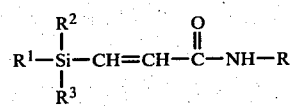

in which $R^1$, $R^2$, $R^3$, and R are as defined above (process a). Compounds I and II have pharmaceutical activity as is described hereinafter under the heading "Statement of Utility".

The above described compounds II are obtainable by reduction of corresponding alkynyl Compounds (III):

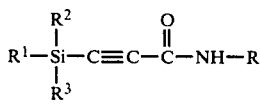   III in which $R^1$, $R^2$, $R^3$ and R are as defined above (process b).

Process (b) may be accomplished by means conventionally employed in converting an alkynyl-bearing compound to its corresponding alkenyl-analog. A convenient method of carrying out process (b) is by treating a compound III with hydrogen in the presence of an appropriate catalyst such as palladium on calcium carbonate (eg 5%), or rhodium, platinum or platinum oxide, on such "controlling" porous supports as calcium carbonate, barium sulfate and the like, in an inert medium, eg a lower alkanol such as ethanol, lower fatty acids and esters, such as acetic acid and ethyl acetate, hydrocarbons, such as benzene or toluene or a cyclic ether such as tetrahydrofuran (THF), at moderate temperatures, for example from about 10° to 80° C. particularly at from about 20° to 30° C., at moderate pressures, eg from about 15 to 100 psi (over atmospheric pressure), eg at 15 psi (over at.).

If desired Compounds III may be converted to their corresponding Compounds I (without recovery of any Compounds II formed during the process, ie process (a')) by means conventionally employed in reducing an alkynyl compound to its corresponding alkyl analog.

Processes (a) and (a') may be accomplished, for example, by hydrogenating under pressures of eg, from about 15 psi to about 100 psi (all over atmospheric pressure), eg 50 psi in the presence of a catalyst such as platinum oxide or other hydrogenation catalysts mentioned in connection with process (b) above, or on active supports, such as charcoal, in an inert medium, such as ethyl acetate, or such media as mentioned in connection with the discussion of process (b) above, and at moderate temperatures, eg 10° to 100° C., particularly at from about 20° to 30° C.

It will be appreciated that by selection of such factors as catalyst, pressure of hydrogen, temperature, and reaction time, optimum yields of the desired compounds I or II may be obtained from corresponding Compounds III, since "total" hydrogenation of the starting alkynyl compound (III) will result in the formation of a corresponding Compound I, while controlled hydrogenation will give predominantly a Compound II. Accordingly, compounds III' ie compounds III in which R is R', will yield corresponding Compounds I' or II'.

Compounds III' are obtainable by reaction of a corresponding organo-metallo Compound of the formula IV:

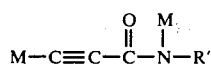   IV in which R' is as defined above and M is an equivalent of an active metal eg an alkali metal or a magnesium halide with a halo-silane of the formula V:

   V in which $R^1$, $R^2$ and $R^3$ are as defined, and Z is halo having an atomic weight of from about 19 to 127, ie fluoro, chloro, bromo or iodo, preferably chloro, (process c), to form an adduct which is then hydrolyzed (process c').

Process (c) is carried out under essentially anhydrous conditions, eg under an atmosphere of inert gas such as dry nitrogen, as are conventionally observed in carrying out Grignard-type reactions, at moderate temperatures, eg −40° to 0° C., in an aprotic medium, eg an ether such as tetrahydrofuran, dimethoxyethane, or a hydrocarbon such as benzene or toluene, which yields an adduct which corresponds to a compound III but in which the "amido" nitrogen atom bears an M-unit (M being as defined above) or a hydrolyzable silyl group corresponding to V, where an excess thereof is used.

The hydrolysis step (process c') may be accomplished in the conventional manner for hydrolyzing a Grignard-type adduct, by treatment with water or a dilute aqueous solution of a salt or acid, eg, saturated aqueous ammonium chloride, at moderate temperatures eg from about 5° to 90° C., preferably at from about 20° to 30° C.

The above-described Compounds IV are obtainable by treatment of a corresponding propiolamide of the formula VI:

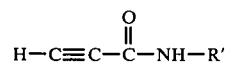   VI in which R' is as defined above, with a M-contributing agent (process d).

Process (d) may be accomplished in the conventional manner for forming organo-metallic reagents by replacing acidic hydrogen atoms of an organic compound with active metal atoms. For example Compounds IV may be obtained by treating the free form of a Compound VI with at least 2 equivalents of M-contributing agent (VII) (preferably at least 3 equivalents where R' is of type (c)) at reduced temperatures, for example Compounds VI and VII may be combined at about −78° to −20° C., eg −60° C., and held at low temperatures with agitation while they are reacting, eg at about −40° to 0° C., eg −20° C., in an aprotic medium, eg an ether, such as THF, dimethoxyethane, or a hydrocarbon, such as hexane, benzene or toluene. Since Compounds IV are decomposed by moisture, it is convenient to employ them directly in Process (c) without recovery, which could involve exposure to moist air, or to maintain them in a conventional stabilizing medium, such as the moisture-free inert aprotic media suitable for use in process (d).

In the M-contributing agents, (Compounds VII), M is an equivalent of an active metal, or a magnesium halide. Active metals include the alkali metals, ie lithium, sodium and potassium, lithium being preferred, while the halo portions of the magnesium halide may be chloro or bromo. A convenient lithium-contributing agent is lithium diisopropylamide (LDA) which may be prepared by reacting n-butyl lithium dissolved in an inert hydrocarbon, such as hexane, with an equivalent of diisopropylamine dissolved in an aprotic solvent, eg THF, at reduced temperatures such as at about $-78°$ to $+25°$ C., eg at $-30°$ C., under essentially anhydrous conditions. It is convenient to prepare the reagent (VII) and use it in situ in process (d).

The above-described propiolamides (VI) are obtainable by amidation of propiolic acid, or an active derivative thereof, with an R'-bearing primary amine of the formula IX:

$$H_2N-R' \qquad (IX)$$

in which R' is as defined above. A convenient method of carrying out such an amidation reaction is by reacting a mixed anhydride of propiolic acid of the formula VIII:

$$H-C\equiv C-\overset{O}{\underset{\|}{C}}-O-\overset{O}{\underset{\|}{C}}-R^6 \qquad VIII$$

in which $R^6$ is lower alkyl having from 1 to 6 carbon atoms, eg ethyl, with a compound IX (process e). The desired compound VIII may be prepared and used in situ, by treating propiolic acid with an equivalent amount (or slight excess) of a non-nucleophilic base, eg an alkali hydride, such as lithium hydride or sodium hydride, or triethylamine, under essentially anhydrous conditions, in an aprotic medium, eg an ether, such as THF, or dimethoxyethane, a hydrocarbon such as benzene or toluene, or a halogenated hdyrocarbon such as methylene chloride or chloroform, at moderate temperatures eg from about 0° to 30° C., preferably from about 20° to 25° C., then slowly introducing into the reaction mixture a chloroformate of the formula X:

$$Cl-\overset{O}{\underset{\|}{C}}-OR^6 \qquad X$$

in which $R^6$ is as defined above, (process e'), at reduced temperatures, eg from about $-20°$ to $-5°$ C., preferably below 10° C., in an aprotic medium such as was used in preparing the reaction mixture, under essentially anhydrous conditions.

The desired amido compound (VI) may be conveniently obtained by slowly adding an amine (IX) to a mixed anhydride, in such aprotic media as described in connection with the preparation of the mixed anhydride (eg in situ) at reduced temperatures, eg from about $-25°$ to 0° C., preferably at from about $-15°$ to 0° C.

The above-described series of reactions may conveniently be represented by Reaction Scheme A below, in which R', $R^1$, $R^2$, $R^3$, $R^6$, Z and M are as defined above to obtain compounds I', II' and III'. However it will be appreciated that in preparing compounds I by the above-described methods, that in those processes which involve hydrogenation, that preliminarily thereto, an unsaturated substrate (II' or III'), in which $R^4$ of the amido moiety is alkyl or benzyl may be hydrolyzed by adapting the above-described procedure for converting a compound Ic' to a compound Ic. Hence a Compound III' (or II') in which $R^4$ is alkyl or benzyl may be converted to its corresponding Compound III (or II) in which $R^4$ is H or a cation, and then hydrogenated to obtain the desired Compound II or I.

Reaction Scheme A

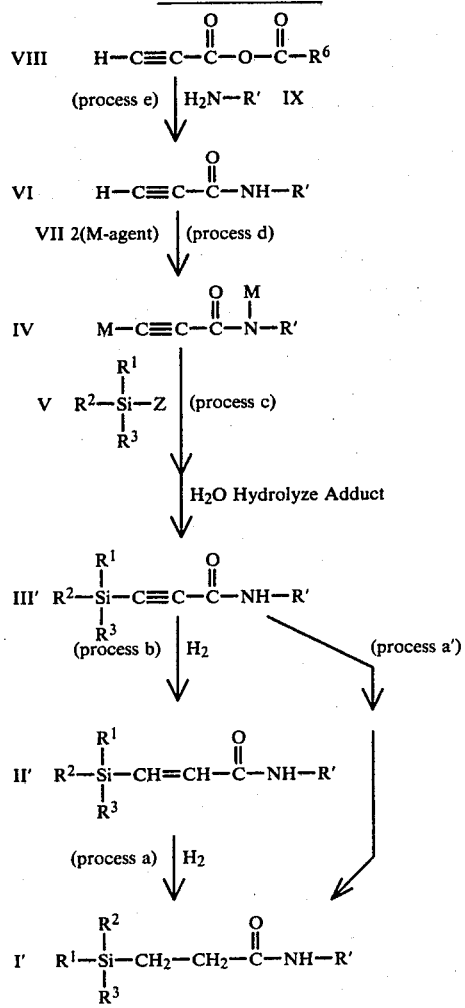

Various modifications of the above-described procedure for obtaining Compounds I and II are possible, and may be conveniently practiced, depending upon such factors as relative availability of starting materials and reagents, scale of production, ease of handling etc. For example, to obtain Compounds III, one may prepare silicon-bearing esters of the formula XI $$\underset{R^2\diagup\phantom{Si}\diagdown R^3}{R^1-Si-C\equiv C-\overset{O}{\underset{\|}{C}}-OR^6} \qquad XI$$

in which $R^1$, $R^2$, $R^3$ and $R^6$ are as defined above, and react such ester (or free acid form thereof), with an amino compound of the formula IXc:

$$H_2NR \qquad (IXc)$$

in which R is as defined above, under conditions conventionally employed in preparing amides.

Alternatively, the acetylenically unsaturated position of an ester compound (XI) as defined above, may be hydrogenated fully to obtain an ester of the formula XII

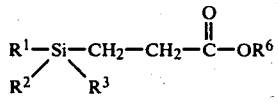

XII in which $R^1$, $R^2$, $R^3$ and $R^6$ are as defined above, and then reacted with an amine IXc to obtain the corresponding final compound I; or partially hydrogenated to obtain a ethylenically unsaturated ester XIII:

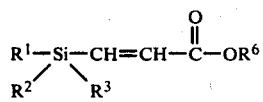

XIII in which $R^1$, $R^2$, $R^3$ and $R^6$ are as defined above, which upon reaction with an amine IXc will yield the corresponding compound II.

An alternative method of preparing Compounds III is by reacting under essentially anhydrous conditions an active metal salt form of propiolic acid of the formula XIV:

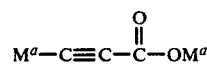

XIV in which $M^a$ is an equivalent of active metal or magnesium halide, with a suitable tri-substituted halo silane (V, as described above) in connection with process (c), in an aprotic medium, at moderate temperatures, eg. 0° to 40°, preferably 20° to 30° C. The same media may be used as mentioned in connection with process (c) to obtain a tri-substituted-silyl-alkynoic acid compound of the formula XV:

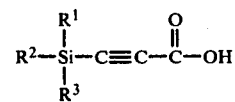

XV in which $R^1$, $R^2$ and $R^3$ are as defined above, which is then reacted with a suitable amine IXc to obtain the corresponding compound III.

If desired, an ester form of propiolic acid may be employed in place of compound XIV, ie of the formula XIV':

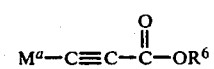

(XIV')

in which $M^a$ and $R^6$ are as defined above.

The above-described alternative procedures may be conveniently represented by Reaction Scheme B, below, in which $R^1$, $R^2$, $R^3$, $R^6$, R, Z, and $M^a$ are as defined above.

Reaction Scheme B,
(Alternative processes)

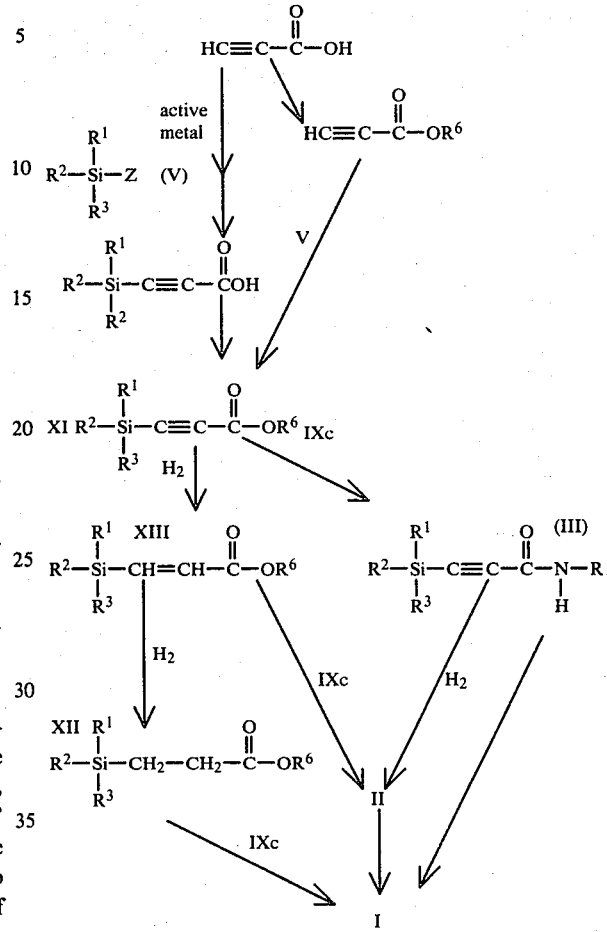

-continued
Reaction Scheme B,
(Alternative processes)

Recovery of the intermediates and products obtained by the above-described procedures may be effected by conventional techniques, such as crystallization, precipitation, vacuum distillation, and chromatographic techniques such as column or thin layer chromatography and the like.

It will be understood that many compounds of this invention, eg I, II and III, may exist in the form of stereoisomers, eg optically active isomers, ie enantiomers, which can be prepared from respective stereoisomers, eg optically active compounds IX or separated and recovered by conventional techniques, eg, resolution and such isomeric forms are also included within the scope of this invention.

Many of the reagents and compounds involved in the above-described procedures are known, eg propiolic acid and compounds V and IX, and may be obtained commercially or may be prepared by methods described in the literature, while those compounds not specifically described in the literature may be prepared by analogous methods from known starting materials.

STATEMENT OF UTILITY

The compounds I and II of this invention are useful as pharmaceutical agents in animals. In particular, the compounds I and II are useful in controlling the cholesterol ester content of mammalian arterial walls and are therefore particularly indicated for use as antiatherosclerotic agents, i.e., agents useful in the prophylatic treatment of atherosclerois and in the controlling of atherosclerotic conditions due to cholesterol ester accumulation in the arterial walls. Such ability of the compounds I and II is indicated by known test procedures in which the total cholesterol ester content of cultured cells is shown to be reduced by a test compound, as compared to untreated cells, and carried out, for example, by the following procedures:

(A) Cell Culture

Rhesus monkey smooth muscle cells (from the arterial, e.g., aorta, wall) obtained by the method of K. Fisher-Dzoga et al. [Experimental and Molecular Pathology 18, 162–176 (1973)] are routinely grown in 75 cm$^2$ tissue culture flasks using Minimum Essential Medium (Eagle) supplemented with 10% fetal bovine serum. For testing a 75 cm$^2$ flask with a near confluent cell growth is selected. The cells are removed from the flask surface by mild enzymatic treatment with pronase. After centrifugation and decanting the enzyme solution, the cell pellet is resuspended in an appropriate volume of media for seeding the desired number of 60 mm tissue culture dishes. Five (5) ml. of the diluted cell suspension are pipetted into each dish. After seeding, the dishes are labelled with the cell type, date and flask number of origin and incubated at 37° C. in approximately 5% $CO_2$ atmosphere in a high humidity incubator. When the cultures are confluent, the actual drug testing is begun. Test compounds are routinely solubilized in 100% ethanol. An equivalent amount of ethanol is added to control groups as well. The tissue culture dishes are randomly divided into groups. To one group, hyperlipemic rabbit serum (HRS) is added at 5% by volume (control). To the remaining groups, 5% HRS and 0.1 to 1 mg. per 100 ml. of media of the test compound are added. The dishes are returned to the incubator for an additional 24 hours. All operations through to the final incubation are performed using sterile technique in a laminar flow hood. After the incubation period, the dishes are microscopically observed with the Zeiss Axiomat with phase contrast optics and the conditions of the cultures are recorded; especially in regard to the size, number and configuration of cytoplasmic inclusions and to cellular morphology. The media is removed from the cultures and 0.9% sodium chloride solution is added. The cells are removed from the flasks with the aid of a rubber policeman and transferred to a conical granuated centrifuge tube. The cells are washed three times by suspending in an isotonic salt solution, centrifuging at 800×g. for 10 minutes and aspirating the supernatant fluid.

(B) Cell Extraction Procedure

An appropriate volume of isopropyl alcohol (about 1 ml/mg. protein) is then added to the cell pellet and the sample sonicated with a micro probe (140×3 mm.) for 10 seconds with a "LO" setting of 50 on a Bronwell Biosonik IV. After contrifugation for 15 minutes at 800×g., the clear supernatant is decanted and an aliquot taken for cholesterol analysis.

The residue is dissolved in 0.1 N sodium hydroxide and an aliquot taken for protein determination by the method of Lowry, et al. (J. Biol. Chem. 193, 265; 1951).

(C) Assay

Free cholesterol: The isopropyl alcoholic solutions of standards, samples and blank (isopropyl alcohol alone) are treated in a similar manner. An aliquot of 0.4 ml. of free agent (Reagent A, Table 1 below) is added to a 10×75 mm. disposable glass test tube to which 20 μl. of the isopropyl alcoholic solution is added and mixed. After standing at room temperature for approximately 2 minutes, 0.8 ml. of 0.5 N sodium hydroxide (Reagent C, Table 1) is added and mixed. The fluorescence is measured with an Aminco-Bowman spectrophotofluorometer with an excitation wavelength of 325 nm and emission wavelength of 415 nm. A 1 cm. light path cuvette is used with a xenon lamp, an IP28 photomultiplier tube and 2 mm slits.

Total cholesterol: The same procedure described above for free cholesterol is followed for total cholesterol except that the total reagent (Reagent B, Table 1) is used instead and the samples are incubated for 20 minutes at 37° C. before the addition of the 0.5 N sodium hydroxide solution (Reagent C, Table 1).

Alternatively, the assay for cholesterol, i.e., Step C (above) obtained from Steps A and B, may be carried out by the method of Ishikawa et al. (J. Lipid Res. 15, 286; 1974).

The amount of cholesterol ester is found by subtracting the amount of free cholesterol from the total cholesterol content of the cells determined by the assay. A finding of a lower amount of cholesterol ester in the group of cells to which test compound was added, as compared to the control group (untreated) shows that the test compound is active in reducing the cholesterol ester in the cells.

TABLE 1

| Composition of Reagents for Cholesterol Determination | | |
|---|---|---|
| A. Free Cholesterol Reagent | | |
| Sodium phosphate buffer pH 7.0 | .05 | M |
| Cholesterol oxidase | .08 | U/ml |
| Horseradish peroxidase | 30.00 | U/ml |
| p-Hydroxyphenylacetic acid | .10 | mg/ml |
| B. Total Cholesterol Reagent | | |
| Sodium phosphate buffer pH 7.0 | .05 | M |
| Cholesterol ester hydrolase | .08 | U/ml |
| Cholesterol oxidase | .08 | U/ml |
| Horseradish peroxidase | 30.00 | U/ml |
| Sodium taurocholate | 5.00 | mM |
| Triton X 100 | .015% | |
| p-Hydroxphenylacetic acid | .15 | mg/ml |
| C. Sodium Hydroxide Solution | .5N | |

Following the above-described test method, comparative test results were carried out and are reported in Tables 2 and 3 below, in which monkey aortic smooth muscle cells were originally obtained from Dr. K. Fisher-Dzoga: Univ. of Chicago, the test compound (Compound A) is (±)-4,4-dimethyl-4-sila-tetradecanoyl-1'-phenyl-2'-p-tolyl-ethylamide of Example 6d administered at 1 μg/ml of media.

TABLE 2

| | | Comparative Test | | | | |
|---|---|---|---|---|---|---|
| | Protein | Cholesterol (μg/mg cell protein) | | | | Percent |
| | | | | Ester | | From |
| Compound | mg/culture | Total | Free | Amount | Mean | Control |
| None | 0.378 | 83.41 | 38.78 | 44.63 | | |
| (Control) | 0.442 | 75.41 | 35.43 | 39.98 | 42.0 | — |
| " | 0.376 | 79.07 | 37.66 | 41.41 | | |
| A | 0.432 | 47.99 | 44.93 | 3.06 | 3.5 | 92* ↓ |
| " | 0.440 | 51.20 | 47.52 | 3.68 | | |
| " | 0.440 | 51.20 | 47.52 | 3.68 | | |

*significant at p less than 0.01

TABLE 3

| Compound | Protein mg/culture | Cholesterol (μg/mg cell protein) | | | | Percent From Control |
|---|---|---|---|---|---|---|
| | | Total | Free | Ester Amount | Mean | |
| None Control | 0.364 | 56.18 | 38.52 | 17.66 | | |
| " | 0.364 | 60.30 | 37.82 | 22.47 | 20.2 | — |
| " | 0.330 | 59.24 | 38.70 | 20.54 | | |
| A | 0.436 | 44.15 | 39.61 | 4.54 | 5.4 | 73* ↓ |
| " | 0.420 | 42.98 | 37.55 | 5.43 | | |
| " | 0.524 | 42.46 | 36.30 | 6.16 | | |

*significant at p less than 0.01

The compounds of the formula I are also indicated as useful as atherosclerotic agents in tests involving oral administration to rabbits at a dose of 15 to 50 mg/kg of the test compound per day for 9 weeks in conjunction with a high cholesterol diet resulting in, compared to controls, a reduction in cholesterol and cholesterol ester serum levels, as well as lessened formation or absence of arterial wall plaques.

When the compounds are employed for the above utility, they may be combined with one or more pharmaceutically acceptable carriers, e.g., solvents, diluents and the like, and may be administered orally in such forms as tablets, capsules, dispersible powders, granules, suspensions containing, for example, from about 0.5 to 5% of suspending agent, syrups containing, for example, from about 20 to 50% ethanol, and the like, or parenterally in the form of sterile injectable solutions or suspensions containing from about 0.5 to 5% suspending agent in an isotonic medium. These pharmaceutical preparations may contain, for example, from about 0.5% up to about 90% of the active ingredient in combination with the carrier, more usually between 5% and 60% by weight.

The antiatherosclerotic effective dosage of active ingredient employed for the reduction of cholesterol ester content in the arterial walls of a mammal may vary depending on the particular compound employed, the mode of administration and the severity of the condition being treated. However, in general, satisfactory results are obtained when the compounds I and II are administered at a daily dosage of from about 0.2 milligrams to about 500 milligrams per kilogram of animal body weight, preferably given in divided doses two to four times a day, or in sustained release form. For most large mammals, the total daily dosage is from about 10 milligrams to about 5,000 milligrams. Dosage forms suitable for internal use comprise from about 2.5 to 2500 milligrams of the active compound in intimate admixture with a solid or liquid pharmaceutically acceptable carrier. Solid carriers include starch, lactose and kaolin, while liquid carriers include sterile water, polyethylene glycols and edible oils such as corn, peanut and sesame oils, as are appropriate to the nature of the active ingredient and the particular form of administration desired. Adjuvants customarily empolyed in the preparation of pharmaceutical compositions may be advantageously included, such as flavoring agents, coloring agents, preserving agents, and antioxidants, e.g., vitamin E, ascorbic acid, BHT and BHA.

The preferred pharmaceutical compositions from the stand-point of ease of preparation and administration are soild compositions, particularly tablets and hard-filled or liquid-filled capsules. When water is a carrier, it is preferred that a suspending agent be present.

Representative formulations for administration orally three times a day prior to feeding in the treatment of atherosclerosis are gelatin capsules prepared by conventional techniques to contain the following:

| Ingredient | Weight (in mg.) | |
|---|---|---|
| (±)-4,4-dimethyl-4-sila-tetradecanoyl-1'-phenyl-2'-p-tolyl-ethylamide | 250 | |
| (±)-4,4-diphenyl-4-sila-n-octanoyl-1'-phenyl-2'-p-tolyl-ethylamide | | 250 |
| corn oil | 500 | 500 |

As is the present understanding in the art, controlling the total cholesterol content of an arterial wall by inhibiting the accumulation thereof by reducing the cholesterol ester content thereof, advantageously inhibits the formation of plaques in the arterial wall.

While the inventor does not wish to be bound by any proposed theory of the mechanism of the action of Compounds I, it has been observed in tests on the compound of Example 6d using the Zilversmit Dual Isotope Method* that the compounds substantially reduce absorption of cholesterol from the gastro-intestinal system of the host, ie at the intestinal wall, possibly by action involving the Acyl Coenzyme A cholesterol acyl transferase (ACAT) enzyme, resulting in a marked reduction of cholesterol intake into the blood of the host, as well as a reduction in the cholesterol content (in free and as ester form) of smooth muscle cells of the host, eg arterial walls, such as those of the aorta and coronary arteries.

*Described in Proc. Soc. Exp. Biol. Med. 140: 862–865 (1972)

The following examples of the preparation of intermediates and compounds I and II of the invention are illustrative of the invention. All temperatures are centigrade (°C.) and room temperature is 20° to 30° C. unless indicated otherwise. It will be understood that the Compounds I, II and III hereinafter described are obtained as mixtures of sterioisomers, unless indicated otherwise.

EXAMPLE 1

4,4-Diphenyl-4-sila-pentanoyl-(1'-phenyl-2'-p-tolyl)ethylamide

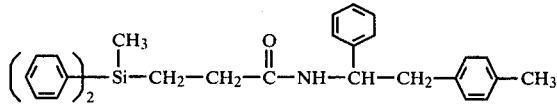

Step A N-[(1'-phenyl-2'-p-tolyl)-ethyl]-propiolamide

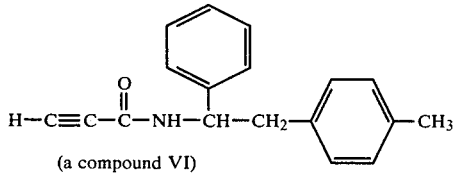

(a compound VI)

95 mg of lithium hydride are added to a solution of 850 mg propiolic acid in 15 ml of freshly distilled THF, portion-wise, over a period of about 45 min., with cooling to avoiding heating over room temperature (hydrogen evolves). The resulting mixture is then cooled to about −10°, and a solution of 1.3 g of ethyl chloroformate in 3 ml of dry THF is added drop-wise with stirring, while maintaining the temperature below −10°. The resulting mixture is then stirred for 2 hrs. at about −15°. A solution of 2.5 g of (1-phenyl 2-p-tolyl) ethylamine in 5 ml of dry THF is then added dropwise at from −15° to 0°, with stirring. The mixture is then stirred at room temperature for 2 hours.

The reaction mixture is concentrated by evaporation in vacuo (solvent stripped) to obtain a residue, which is taken up in methylene chloride and is washed first with dilute aqueous sodium bicarbonate, then with dilute hydrochloric acid, then dried over anh. sodium sulfate, and concentrated in vacuo to obtain crude product. The crude product of this step is refined by crystallizing from diethyl ether m.p. 152°–155° C.

Step B
4,4-Diphenyl-4-sila-pent-2-ynoyl-(1′-phenyl-2′-p-tolyl)-ethylamide (a Compound III)

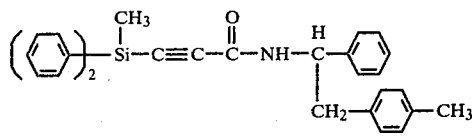

In a vessel, under an atmosphere of dry nitrogen at −30° 460 mg of n-butyl lithium in 10 ml of dry hexane is added to 300 mg of diisopropylamine in 15 ml of dry THF. The mixture stirred for 15 min., then cooled to −60°. A solution of 600 mg of [(1′-phenyl-2′-p-tolyl)-ethyl] propiolamide in 10 ml of dry THF is added dropwise thereto while the temperature of the mixture is maintained below −50°. The mixture is then stirred for 1 hr. at −20°. A solution of 550 mg of diphenyl-methyl-chlorosilane in 3 ml of dry THF is added dropwise, with stirring and the mixture stirred for 90 min (at −20°).

Aqueous saturated ammonium chloride is added to the reaction mixture, and the organic phase recovered, dried over anh. sodium sulfate, and concentrated by evaporation in vacuo to obtain the crude product as an oil, which is refined by eluting through a silica gel column using chloroform as eluate to yield the product of this step as an oil.

Step C
4,4-diphenyl-4-sila-pentanoyl-1′-phenyl-2′-p-tolylethylamide (a Compound I)

To a solution of 300 mg of 4,4-diphenyl-4-sila-pent-2-ynoyl-(1′-phenyl-2′-p-tolyl)-ethylamide in 30 ml of ethyl acetate in a hydrogenating apparatus, is added 50 mg of platinum oxide, and a pressure of 50 p.s.i. hydrogen is maintained for 24 hours with shaking. The reaction mixture is the filtered, and the filtrate concentrated (by evaporation in vacuo) to obtain the title product as an oil.

EXAMPLE 2
4,4-Dimethyl-4-sila-pent-2-enoyl-(1′-phenyl-2′-p-tolyl)-ethylamide (a Compound II)

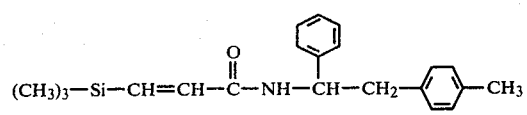

Step A & B
4,4-dimethyl-sila-pent-2-ynol-(1′-phenyl-2′-p-tolyl)-ethylamide (a Compound III)

Repeating the procedure of Steps A and B of Example 1, but using in place of the diphenylmethylchlorosilane used (in Step B) therein, an approximately equivalent amount of trimethylchlorosilane, there is accordingly obtained 4,4-dimethyl-4-sila-pent-2-ynoyl-(1′-phenyl-2′-p-tolyl)-ethylamide (m.p. 118°–120°).

Step C
4,4-dimethyl-4-sila-pent-2-enoyl-(1′-phenyl-2′-p-tolyl)-ethylamide

To a solution of 335 mg of 4,4-dimethyl-4-sila-pent-2-ynoyl-(1′-phenyl-2′-p-tolyl)-ethylamide in 25 ml of ethanol in a hydrogenating apparatus, is added 50 mg of 5% palladium on calcium carbonate. The mixture is placed under 1 at. pressure of hydrogen and shaken until an equivalent of hydrogen gas had been taken up (about 45 min.). The reaction mixture is then filtered, and the filtrate concentrated (by evaporation in vacuo) to obtain the title product as an oil.

EXAMPLE 3
4,4-Dimethyl-4-sila-pentanoyl-(1′-phenyl-2′-p-tolyl)-ethylamide

Treating 4,4-dimethyl-4-sila-pent-2-enoyl-(1′-phenyl-2′-p-tolyl)-ethylamide (obtained by Example 2) by the procedure of Step C of Example 1, the title product is obtained.

EXAMPLE 4

Following the procedure of steps A and B of Example 1, but using in place of the diphenylmethylchlorosilane used therein, an approximately equivalent amount of the following compounds V:
(a) dimethyl, n-propyl,chlorosilane;
(b) dimethyl, n-octyl,chlorosilane;
(c) t-butyl, dimethyl,chlorosilane;
(d) dimethyl, n-decyl,chlorosilane
(e) dimethyl, phenyl, chlorosilane;
(f) diphenyl, methyl, bromosilane;
(g) benzyl, dimethyl, chlorosilane;
(h) dibenzyl, methyl chlorosilane;
(i) benzyl, methyl, phenyl, chlorosilane;
(j) dimethyl, p-tolyl-chlorosilane;
(k) diphenyl, n-octyl chlorosilane;
(l) triphenyl, chlorosilane;
(m) diphenyl, n-butyl chlorosilane;
(n) n-butyl-diethyl chlorosilane; or
(o) dimethyl-n-octadecyl, chlorosilane;
there is accordingly obtained the corresponding compound III respectively:
(a) 4,4-dimethyl-4-sila-n-hept-2-ynoyl-(1′-phenyl-2-tolyl)-ethylamide;
(b) 4,4-dimethyl-4-sila-n-dodec-2-ynoyl-(1′-phenyl-2-p-tolyl)-ethylamide;
(c) 4-t-butyl-4-methyl-4-sila-pent-2-ynoyl-(1′-phenyl-2-p-tolyl)-ethylamide;
(d) 4,4-dimethyl-4-sila-n-tetradec-2-ynoyl-(1′-phenyl-2′-p-tolyl)-ethylamide;
(e) 4-methyl-4-phenyl-4-sila-pent-2-ynoyl-(1′-phenyl-2′-p-tolyl)-ethylamide;
(f) 4,4-diphenyl-4-sila-pent-2-ynoyl-(1′-phenyl-2′-p-tolyl)ethylamide;

(g) 4,4-dimethyl-5-phenyl-4-sila-pent-2-ynoyl-(1'-phenyl-2'-p-tolyl)ethylamide (as an oil);
(h) 4,4-dibenzyl-4-sila-pent-2-ynoyl-(1'-phenyl-2'-p-tolyl)ethylamide;
(i) 4-benzyl-4-phenyl-4-sila-pent-2-ynoyl-(1'-phenyl-2'-p-tolyl)ethylamide;
(j) 4-methyl-4p-tolyl-4-sila-pent-2-ynoyl-(1'-phenyl-2'-p-tolyl)ethylamide;
(k) 4,4-diphenyl-4-sila-n-dodec-2-ynoyl-(1'-phenyl-2'-p-tolyl)ethylamide;
(l) 4,4,4-triphenyl-4-sila-but-2-ynoyl-(1'-phenyl-2'-p-tolyl)ethylamide;
(m) 4,4-diphenyl-4-sila-n-oct-2-ynoyl-(1'-phenyl-2'-p-tolyl)ethylamide;
(n) 4,4-diethyl-4-sila-n-oct-2-ynoyl-(1'-phenyl-2'-p-tolyl)ethylamide, and
(o) 4,4-dimethyl-sila-n-dodec-2-ynoyl(1'-phenyl-2'-p-tolyl)ethylamide.

EXAMPLE 5

Repeating the procedure of step C of Example 2, but using in place of the 4,4-dimethyl-4-sila-pent-2-nyoyl-(1'-phenyl-2'-p-tolyl)-ethylamide used therein, an approximately equivalent amount of each of the products (a) to (o) of Example 4, there is accordingly obtained, respectively, the corresponding compounds II:
(a) 4,4-dimethyl-4-sila-n-hept-2-enoyl-(1'-phenyl-2'-p-tolyl)-ethylamide;
(b) 4,4-dimethyl-4-sila-n-dodec-2-enoyl-(1'-phenyl-2'-p-tolyl)-ethylamide;
(c) 4-t-butyl-4-methyl-4-sila-pent-2-enoyl-(1'-phenyl-2-p-tolyl)-ethylamide*;

*may also be called 4,4,5,5-tetramethyl-n-hex-2-enoyl-(1'-phenyl-2'-p-tolyl)ethylamide.

(d) 4,4-dimethyl-4-sila-n-tetradec-2-enoyl-(1'-phenyl-2'-p-tolyl)-ethylamide;
(e) 4-methyl-4-phenyl-4-sila-pent-2-enoyl-(1'-phenyl-2'-p-tolyl)-ethylamide;
(f) 4,4-diphenyl-4-sila-pent-2-enoyl-(1'-phenyl-2'-p-tolyl)ethylamide;
(g) 4,4-dimethyl-5-phenyl-4-sila-pent-2-enoyl-(1'-phenyl-2'-p-tolyl)ethylamide;
(h) 4,4-dibenzyl-4-sila-pent-2-enoyl-(1'-phenyl-2'-p-tolyl)ethylamide;
(i) 4-benzyl-4-phenyl-4-sila-pent-2-enoyl-(1'-phenyl-2'-tolyl)ethylamide;
(j) 4-methyl-4-p-tolyl-4-sila-pent-2-enoyl-(1'-phenyl-2'-p-tolyl)ethylamide.
(k) 4,4-diphenyl-4-sila-n-dodec-2-enoyl-(1'-phenyl-2'-p-tolyl)ethylamide;
(l) 4,4,4-triphenyl-4-sila-but-2-enoyl-(1'-phenyl-2'-p-tolyl)ethylamide;
(m) 4,4-diphenyl-4-sila-n-oct-2-enoyl-(1'-phenyl-2'-p-tolyl)ethylamide (as a wax);
(n) 4,4-diethyl-4-sila-n-oct-2-enoyl-(1'-phenyl-2'-p-tolyl)ethylamide; and
(o) 4,4-dimethyl-4-sila-n-dodec-2-enoyl-(1'-phenyl-2'-p-tolyl)ethylamide.

EXAMPLE 6

Repeating the procedure of Step C of Example 1 using in place of the 4,4-diphenyl-4-sila-pent-2-ynoyl-(1'-phenyl-2-p-tolyl)ethylamide used therein, an approximately equivalent amount of the products a to o of Example 5 there is accordingly obtained respectively the corresponding compounds Ia:
(a) 4,4-dimethyl-4-sila-n-heptanoyl-(1'-phenyl-2'-p-tolyl)-ethylamide, (as an oil);
(b) 4,4-dimethyl-4-sila-n-dodecanoyl-(1'-phenyl-2'-p-tolyl)-ethylamide, (as an oil);
(c) 4-t-butyl-4-methyl-4-sila-pentanoyl-(1'-phenyl-2-p-tolyl)-ethylamide, (as an oil);
(d) 4,4-dimethyl-4-sila-n-tetradecanoyl-(1'-phenyl-2'-p-tolyl)-ethylamide (m.p. 39°–42°);
(e) 4-methyl-4-phenyl-4-sila-pentanoyl-(1'-phenyl-2'-p-tolyl)-ethylamide, (as a gum);
(f) 4,4-diphenyl-4-sila-pentanoyl-(1'-phenyl-2'-p-tolyl)ethylamide, (as an oil);
(g) 4,4-dimethyl-5-phenyl-4-sila-pentanoyl-(1'-phenyl-2'-p-tolyl)ethylamide, (as an oil);
(h) 4,4-dibenzyl-4-sila-pentanoyl-(1'-phenyl-2'-p-tolyl)ethylamide;
(i) 4-benzyl-4-phenyl-4-sila-pentanoyl-(1'-phenyl-2'-p-tolyl)ethylamide;
(j) 4-methyl-4-p-tolyl-4-sila-pentanoyl-(1'-phenyl-2'-p-tolyl)ethylamide;
(k) 4,4-diphenyl-4-sila-n-dodecanoyl-(1'-phenyl-2'-p-tolyl)ethylamide;
(l) 4,4,4-triphenyl-4-sila-butanoyl-(1'-phenyl-2'-p-tolyl)ethylamide;
(m) 4,4-diphenyl-4-sila-n-octanoyl-(1'-phenyl-2'-p-tolyl)ethylamide (mp 92°–97°);
(n) 4,4-diethyl-4-sila-n-octanoyl-(1'-phenyl-2'-p-tolyl)ethylamide (as an oil); and
(o) 4,4-dimethyl-4-sila-n-dodecanoyl-(1'-phenyl-2'-p-tolyl)ethylamide, (mp 64°–5°).

EXAMPLE 7

N-4,4-Dimethyl-4-sila-pentanoyl-benzylamide

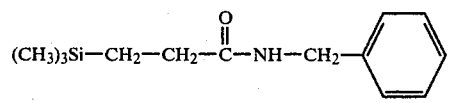

Adapting the procedure of Example 2, but using in place of the (1'-phenyl-2'-p-tolyl)-ethylamine used therein, benzylamine, there is obtained from steps A+B, N-4,4-dimethyl-4-sila-pent-2-ynoyl-benzylamide (m.p. 73°–76°), and from Step C, N-4,4-dimethyl-4-sila-pent-2-enoylbenzylamide (m.p. 68°–72°), which by treatment by the procedure of Step C of Example 1, the title product is obtained (as an oil).

EXAMPLE 8

Repeating the procedure of steps A and B of Example 1, but using in place of the (1-phenyl-2-p-tolyl)ethylamine used in Step A, therein, an approximately equivalent amount of the following amines as compounds IX:
(a) 1-amino-indane;
(b) DL-tryptophan ethyl ester, hydrochloride;
(c) (d,l) α-methylbenzylamine; (racemate);
(d) 2-methylaniline; or
(e) 1-benzyl-2-phenylethylamine; there is accordingly obtained, respectively (as compounds III):
(a) N-(4,4-diphenyl-4-sila-pent-2-ynoyl)-1-indanylamide;
(b) N-(4,4-diphenyl-4-sila-pent-2-ynoyl)-tryptophan, ethyl ester;
(c) N-(4,4-diphenyl-4-sila-pent-2-ynoyl)-α-methylbenzylamide; (as a mixture of racemates, m.p. 34°);
(d) N-(4,4-diphenyl-4-sila-pent-2-ynoyl)-o-methylphenylamide; and
(e) N-(1'-benzyl-2'-phenyl)ethyl-4,4-diphenyl-4-sila-penta-2-ynoylamide.

EXAMPLE 9

Repeating the procedure of Step C Example 2, above, but using in place of the 4,4-dimethyl-4-sila-pent-2-ynoyl-(1'-phenyl-2'-p-tolyl)-ethylamide used therein, an approximately equivalent amount of each of the products of Example 8, there is accordingly obtained (as compounds II) there is accordingly obtained, respectively:

(a) N-(4,4-diphenyl-4-sila-pent-2-enoyl)-1-indanylamide;
(b) N-(4,4-diphenyl-4-sila-pent-2-enoyl)-tryptophan, ethyl ester;
(c) N-(4,4-diphenyl-4-sila-pent-2-enoyl)-α-methyl-benzylamide, (as a racemic mixture);
(d) N-(4,4-diphenyl-4-sila-pent-2-enoyl)-o-methylphenylamide; and
(e) N-(1'-benzyl-2'-phenyl)ethyl-4,4-diphenyl-4-sila-penta-2-enoylamide.

EXAMPLE 10

Repeating the procedure of step C of Example 1, but using in place of the 4,4-diphenyl-4-sila-pent-2-ynoyl-(1-phenyl-2-p-tolyl)ethylamide used therein, an approximately equivalent amount of the products of Example 9, there is accordingly obtained, respectively:

(a) N-(4,4-diphenyl-4-sila-pentanoyl)-1-indanylamide;
(b) N-(4,4-diphenyl-4-sila-pentanoyl)-tryptophan, ethyl ester;
(c) N-(4,4-diphenyl-4-sila-pentanoyl)-α-methylbenzylamide, (as a racemic mixture);
(d) N-(4,4-diphenyl-4-sila-pentanoyl)-o-methylphenylamide; and
(e) N-(1'-benzyl-2'-phenyl)ethyl-4,4-diphenyl-4-sila-pentanoylamide.*

*may also be called 4,4-diphenyl-4-sila-n-pentanoyl-(1'-benzyl-2'-phenyl)ethylamide.

EXAMPLE 11

Repeating the procedures of Examples 2 and 3 but using in place of the trimethylchlorosilane, used in Example 2, an approximately equivalent amount of dimethyl, n-decyl chlorosilane, and in place of the (1-phenyl-2-p-tolyl)ethylamine used in Example 2, an approximately equivalent amount of the following amines as Compounds IX:

(a) 1-amino-indane;
(b) DL-tryptophan ethyl ester, hydrochloride;
(c) (d,l) α-methylbenzylamine; (racemate);
(d) 2-methylaniline;
(e) (1-benzyl-2-phenyl)ethylamine;
(f) (+)-α-methylbenzlamine;
(g) (+)-(1-phenyl-2-p-tolyl)ethylamine; or
(h) (−)-(1-phenyl-2-p-tolyl)ethylamine;
there is accordingly obtained, respectively:

(a) N-(4,4-dimethyl-4-sila-tetradecanoyl)-1-indanylamide;
(b) N-4,4-dimethyl-4-sila-tetradecanoyl-tryptophan, ethyl ester, (m.p. 54°);
(c) N-(4,4-dimethyl-4-sila-tetradecanoyl)-α-methylbenzylamide, (as a racemic mixture);
(d) N-(4,4-dimethyl-4-sila-tetradecanoyl)-o-methylphenylamide;
(e) N-(1-benzyl-2-phenyl)ethyl-(4,4-dimethyl-4-sila-tetradecanoylamide (m.p. 70°-71°);
(f) (+)N-(4,4-dimethyl-4-sila-tetradecanoyl-1'-phenylethylamide (as an oil);
(g) (+)N-4,4-dimethyl-4-sila-tetradecanoyl-(1'-phenyl-2'-p-tolyl)ethylamide (as an oil); and
(h) (−)N-4,4-dimethyl-4-sila-tetradecanoyl-(1'-phenyl-2'-p-tolyl)ethylamide (as an oil).

EXAMPLE 12

4-(o-methoxyphenyl)-4-methyl-4-sila-pentanoyl-(1'-benzyl-2'-phenyl)ethylamide

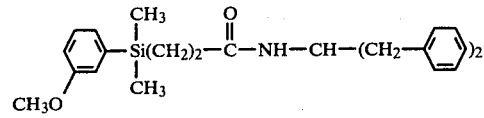

Following the procedure of Example 1, but in the first step, using in place of the (1-phenyl-2-p-tolyl) ethylamine, using an approximately equivalent amount of 1-benzyl 2-phenyl)ethylamine; and in the second step using in place of the diphenyl-methylchlorosilane using an approximately equivalent amount of o-methoxyphenyl-dimethylchlorosilane, there is accordingly obtained the title product, m.p. 75°.

EXAMPLE 13

4,4-dimethyl-4-sila-4-dodecanoyl-α-methyl-benzylamide

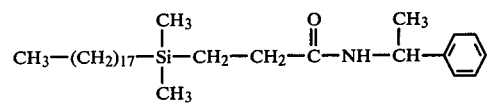

Following the procedure of Example 1, but in the first step using in place of the (1-phenyl-2-p-tolyl)ethylamine, using an approximately equivalent amount of α-methylbenzylamine; and in the second step using in place of the diphenyl-methylchlorosilane using an approximately equivalent amount of dimethyl-n-octadecyl-chlorosilane there is accordingly obtained the title product, m.p. 61°.

What is claimed is:

1. A compound of the formula:

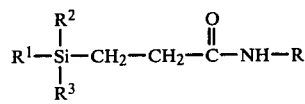

wherein each of
R$^1$, R$^2$ and R$^3$ is, independently, alkyl having from 1 to 22 carbon atoms; or a radical of the formula

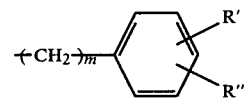

in which
m is 0, 1 or 2, and each of R' and R" is independently a hydrogen atom, alkyl having from 1 to 3 carbon atoms, alkoxy having from 1 to 3 carbon atoms, or halo having an atomic weight of from about 19 to 127; and R is a an aralkyl-type radical of the formula (a), (c) or (d)

(a)

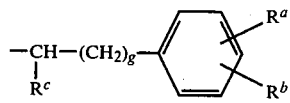

wherein
g is 0, 1 or 2;
$R^a$ is a hydrogen atom, halo having an atomic weight of from about 19 to 127, alkoxy having from 1 to 4 carbon atoms, or alkyl having from 1 to 4 carbon atoms, or trifluoromethyl;
$R^b$ is a hydrogen atom, alkyl having from 1 to 3 carbon atoms, alkoxy having from 1 to 3 carbon atoms, or halo having an atomic weight of from about 19 to 36; and
$R^c$ is subtype (i) a hydrogen atom; subtype (ii), a radical of the structure (ii)

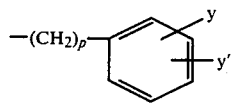

in which
p is 0, 1 or 2, and
y is a hydrogen atom, halo having an atomic weight of from about 19 to 127, alkoxy having from 1 to 4 carbon atoms, or alkyl having from 1 to 4 carbon atoms; and
y' is a hydrogen atom, alkoxy having from 1 to 3 carbon atoms, alkyl having from 1 to 3 carbon atoms, or halo having an atomic weight of from about 19 to 36; or subtype (iii) alkyl having from 1 to 8 carbon atoms; or (c)

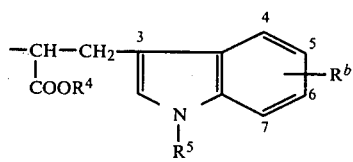

wherein
$R^b$ is as defined above;
$R^4$ is hydrogen; an equivalent of a cation which results in the formation of a salt which is pharmaceutically acceptable; alkyl having from 1 to 8 carbon atoms; or benzyl;
$R^5$ is a hydrogen atom, alkyl having from 1 to 8 carbon atoms or benzyl; or (d)

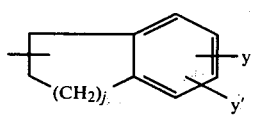

wherein
y and y' are as defined above; and
j is a whole integer of from 1 to 4;
providing that at least one of $R^1$, $R^2$ and $R^3$ is of the formula

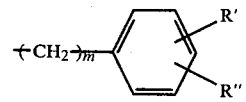

2. A compound of the formula:

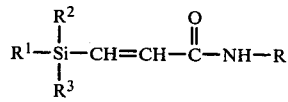

wherein each of $R^1$, $R^2$ and $R^3$ is, independently alkyl having from 1 to 22 carbon atoms; or a radical of the formula

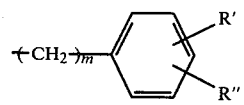

in which
m is 0, 1 or 2, and each of R' and R" is independently a hydrogen atom, alkyl having from 1 to 3 carbon atoms, alkoxy having from 1 to 3 carbon atoms, or halo having an atomic weight of from about 19 to 127; and R is a radical of the formula (a), (b), (c) or (d)

(a)

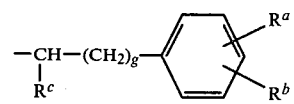

wherein
g is 0, 1 or 2;
$R^a$ is a hydrogen atom, halo having an atomic weight of from about 19 to 127, alkoxy having from 1 to 4 carbon atoms, or alkyl having from 1 to 4 carbon atoms, or trifluoromethyl;
$R^b$ is a hydrogen atom, alkyl having from 1 to 3 carbon atoms, alkoxy having from 1 to 3 carbon atoms, or halo having an atomic weight of from about 19 to 36; and
$R^c$ is subtype (i) a hydrogen atom; subtype (ii), a radical of the structure (ii)

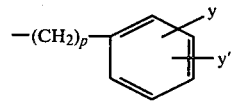

in which
p is 0, 1 or 2, and
y is a hydrogen atom, halo having an atomic weight of from about 19 to 127, alkoxy having from 1 to 4 carbon atoms, or alkyl having from 1 to 4 carbon atoms; and
y' is a hydrogen atom, alkoxy having from 1 to 3 carbon atoms, alkyl having from 1 to 3 carbon atoms, or halo having an atomic weight of from about 19 to 36; or subtype (iii) alkyl having from 1 to 8 carbon atoms;

(b)

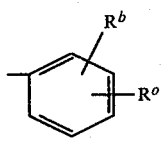

in which
$R^b$ is as defined above, and
$R^o$ is a hydrogen atom, halo having an atomic weight of from about 19 to 127, alkoxy having from 1 to 4 carbon atoms, or alkyl having from 1 to 4 carbon atoms; or
$R^o$ is a radical of the structure $R^f$:

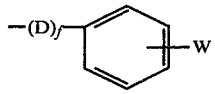

in which
D is —CH$_2$— or —O—;
f is 0 or 1; and
W is a hydrogen atom, halo having an atomic weight of from about 19 to 80, alkoxy having from 1 to 3 carbon atoms, or alkyl having from 1 to 3 carbon atoms; or (c)

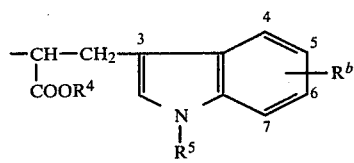

wherein
$R^b$ is as defined above;
$R^4$ is hydrogen; an equivalent of a cation which results in the formation of a salt which is pharmaceutically acceptable; alkyl having from 1 to 8 carbon atoms; or benzyl;
$R^5$ is a hydrogen atom, alkyl having from 1 to 8 carbon atoms or benzyl; or (d)

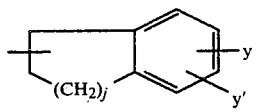

wherein
y and y' are as defined above; and
j is a whole integer of from 1 to 4.

3. A pharmaceutical composition suitable for reducing the cholesterol ester content of an arterial wall of a mammal comprising a cholesterol ester-reducing effective amount of a compound of claim 1 and a non-toxic pharmaceutically-acceptable carrier.

4. A method of reducing the cholesterol ester content of an arterial wall, in a mammal in need of such treatment, comprising administering a total cholesterol ester-reducing amount of a compound of claim 2 to said mammal.

5. A pharmaceutical composition suitable for reducing the cholesterol ester content of an arterial wall of a mammal comprising a cholesterol ester-reducing effective amount of a compound of claim 2 and a non-toxic pharmaceutically-acceptable carrier.

6. A process for the preparation of a compound of the formula:

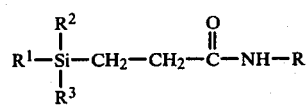

in which R, $R^1$, $R^2$ and $R^3$ are as defined in claim 1, which comprises reducing a compound of the formula:

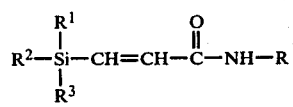

in which R, $R^1$, $R^2$ and $R^3$ are as defined above.

7. A process for the preparation of a compound of the formula

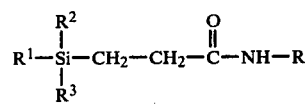

in which R, $R^1$, $R^2$ and $R^3$ are as defined in claim 1, which comprises reducing a compound of the formula

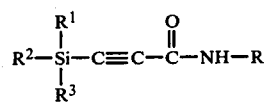

in which R, $R^1$, $R^2$ and $R^3$ are as defined above.

8. A process for the preparation of a compound of the formula:

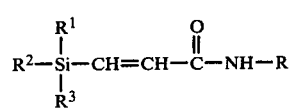

in which R, $R^1$, $R^2$ and $R^3$ are as defined in claim 2, which comprises reducing a compound of the formula:

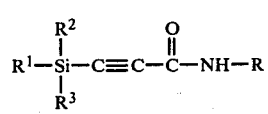

in which R, $R^1$, $R^2$ and $R^3$ are as defined above.

9. A compound of the formula:

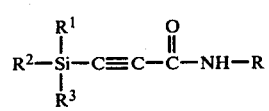

wherein each of R¹, R² and R³ is, independently alkyl having from 1 to 22 carbon atoms; or a radical of the formula

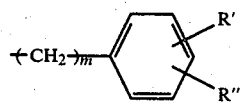

in which m is 0, 1 or 2, and each of R' and R" is independently a hydrogen atom, alkyl having from 1 to 3 carbon atoms, alkoxy having from 1 to 3 carbon atoms, or halo having an atomic weight of from about 19 to 127; and R is a radical of the formula (a), (b), (c) or (d)

(a)

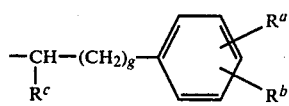

wherein g is 0, 1 or 2;

$R^a$ is a hydrogen atom, halo having an atomic weight of from about 19 to 127, alkoxy having from 1 to 4 carbon atoms, or alkyl having from 1 to 4 carbon atoms, or trifluoromethyl;

$R^b$ is a hydrogen atom, alkyl having from 1 to 3 carbon atoms, alkoxy having from 1 to 3 carbon atoms, or halo having an atomic weight of from about 19 to 36; and $R^c$ is subtype (i) a hydrogen atom; subtype (ii), a radical of the structure (ii)

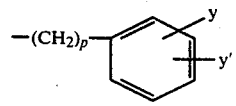

in which p is 0, 1 or 2, and y is a hydrogen atom, halo having an atomic weight of from about 19 to 127, alkoxy having from 1 to 4 carbon atoms, or alkyl having from 1 to 4 carbon atoms; and y' is a hydrogen atom, alkoxy having from 1 to 3 carbon atoms, alkyl having from 1 to 3 carbon atoms, or halo having an atomic weight of from about 19 to 36; or subtype (iii) alkyl having from 1 to 8 carbon atoms;

(b)

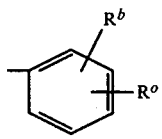

in which $R^b$ is as defined above, and $R^o$ is a hydrogen atom, halo having an atomic weight of from about 19 to 127, ie. alkoxy having from 1 to 4 carbon atoms, or alkyl having from 1 to 4 carbon atoms; or a radical of formaul $R^f$:

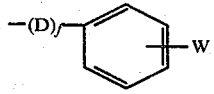

in which

D is —CH₂— or —O—;

f is 0 or 1; and

W is a hydrogen atom, halo having an atomic weight of from about 19 to 80, alkoxy having from 1 to 3 carbon atoms, or alkyl having from 1 to 3 carbon atoms; or (c)

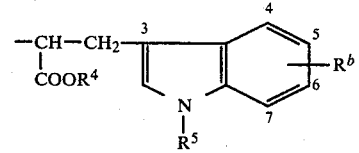

wherein $R^b$ is as defined above;

$R^4$ is hydrogen; an equivalent of a cation which results in the formation of a salt which is pharmaceutically acceptable; alkyl having from 1 to 8 carbon atoms; or benzyl;

$R^5$ is a hydrogen atom, alkyl having from 1 to 8 carbon atoms or benzyl; or (d)

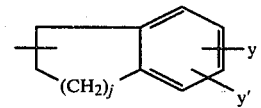

wherein y and y' are as defined above; and j is a whole integer of from 1 to 4.

10. A process for the preparation of a compound of the formula:

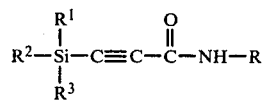

in which R, R¹, R² and R³ are as defined in claim 9, provided that when R is of type (c) then R⁴ is alkyl or benzyl which comprises the steps of (a) reacting a dianion of the formula:

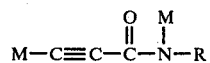

in which R is as defined, and M is an equivalent of an active metal or a magnesium chloride or bromide with a tri substituted-halo silane of the formula

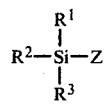

in which $R^1$, $R^2$ and $R^3$ are as defined, and Z is halo having an atomic weight of from about 19 to 127, to form an adduct; and (b) hydrolyzing said adduct.

11. A compound of claim 1, 2, or 9 in which R is of formula (a).

12. A compound of claim 2, or 9 in which R is of formula (b).

13. A compound of claim 1, 2, or 9 in which R is of formula (c).

14. A compound of claim 1, 2, or 9 in which R is of formula (d).

15. The compound of claim 1 which is 4-methyl-4-phenyl-4-sila-pentanoyl-(1'-phenyl-2'-p-tolyl)-ethylamide.

16. The compound of claim 1 which is 4,4-diphenyl-4-sila-pentanoyl-(1'-phenyl-2'-p-tolyl)ethylamide.

17. A compound of claim 1 which is 4,4-dimethyl-5-phenyl-4-sila-pentanoyl-(1'-phenyl-2'-p-tolyl)ethylamide.

18. The compound of claim 1 which is 4,4-diphenyl-4-sila-n-octanoyl-(1'-phenyl-2'-p-tolyl)ethylamide.

19. The compound of claim 1, which is 4-(o-methoxyphenyl)-4-methyl-4-sila-pentanoyl-(1'-benzyl-2'-phenyl) ethylamide.

20. A compound of claim 1, 2 or 9 in which two of $R^1$, $R^2$ and $R^3$ are the same.

21. A compound of claim 1, 2 or 9 in which $R^2$ and $R^3$ are of type (b).

22. A compound of claim 1, 2 or 9 in which $R^2$ and $R^3$ are methyl.

23. A compound of claim 1, 2 or 9 in which R is 1-phenyl 2-(p-tolyl)ethyl.

24. The compound of claim 2 which is 4,4-dimethyl-4-sila-pent-2-enoyl-(1'-phenyl-2'-p-tolyl)-ethylamide.

25. A compound of claim 2 which is N-4,4-dimethyl-4-sila-pent-2-enoyl-benzylamide.

26. A compound of claim 2 which is 4,4-diphenyl-4-sila-n-oct-2-enoyl-(1'-phenyl-2'-p-tolyl)ethylamide.

27. The compound of claim 9 which is 4,4-diphenyl-4-sila-pent-2-ynoyl-(1'-phenyl-2'-tolyl)ethylamide.

28. The compound of claim 9 which is 4,4-dimethyl-4-sila-pent-2-ynoyl-(1'-phenyl-2'-tolyl)ethylamide.

29. A compound of claim 1, 2 or 9 provided that when R is of type (c), then $R^4$ is alkyl or benzyl.

30. A method of reducing the cholesterol ester content of an arterial wall in a mammal in need of such treatment, comprising administering to said mammal a total cholesterol ester-reducing amount of a compound of the formula $$R^1-\underset{\underset{R^3}{|}}{\overset{\overset{R^2}{|}}{Si}}-CH_2-CH_2-\overset{\overset{O}{\|}}{C}-NHR$$

wherein each of $R^1$, $R^2$ and $R^3$ is, independently, alkyl having from 1 to 22 carbon atoms; or a radical of the formula $$-(CH_2)_m-\underset{R''}{\overset{R'}{\diagdown}}\!\!\!\!\!\!\bigcirc$$

in which m is 0, 1 or 2, and each of R' and R" is independently a hydrogen atom, alkyl having from 1 to 3 carbon atoms, alkoxy having from 1 to 3 carbon atoms, or halo having an atomic weight of from about 19 to 127; and R is a radical of formula (a), (b), (c) or (d)

(a)

$$-\underset{R^c}{\overset{}{C}H}-(CH_2)_g-\underset{R^b}{\overset{R^a}{\diagdown}}\!\!\!\!\!\!\bigcirc$$

wherein
g is 0, 1 or 2;
$R^a$ is a hydrogen atom, halo having an atomic weight of from about 19 to 127, alkoxy having from 1 to 4 carbon atoms, or alkyl having from 1 to 4 carbon atoms, or trifluoromethyl;
$R^b$ is a hydrogen atom, alkyl having from 1 to 3 carbon atoms, alkoxy having from 1 to 3 carbon atoms, or halo having an atomic weight of from about 19 to 36; and
$R^c$ is subtype (i) a hydrogen atom; subtype (ii) a radical of the structure (ii)

$$-(CH_2)_p-\underset{y'}{\overset{y}{\diagdown}}\!\!\!\!\!\!\bigcirc$$

in which
p is 0, 1 or 2, and
y is a hydrogen atom, halo having an atomic weight of from about 19 to 127, alkoxy having from 1 to 4 carbon atoms, or alkyl having from 1 to 4 carbon atoms; and
y' is a hydrogen atom, alkoxy having from 1 to 3 carbon atoms, alkyl having from 1 to 3 carbon atoms, or halo having an atomic weight of from about 19 to 36; or subtype (iii) alkyl having from 1 to 8 carbon atoms;

(b)

$$-\underset{R^o}{\overset{R^b}{\diagdown}}\!\!\!\!\!\!\bigcirc$$

in which
$R^b$ is as defined above, and
$R^o$ is a hydrogen atom, halo having an atomic weight of from about 19 to 127, alkoxy having from 1 to 4 carbon atoms, or alkyl having from 1 to 4 carbon atoms; or a radical of the structure $R^f$:

$$-(D)_f-\underset{}{\overset{}{\bigcirc}}\!\!\!\!\!\!-W$$

in which
D is $-CH_2-$ or $-O-$;
f is 0 or 1; and
W is a hydrogen atom, halo having an atomic weight of from about 19 to 80, alkoxy having from 1 to 3 carbon atoms, or alkyl having from 1 to 3 carbon atoms;

(c)

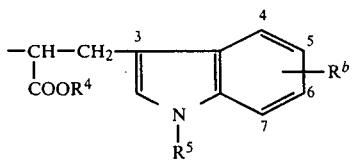

wherein $R^b$ is as defined above;

$R^4$ is hydrogen; an equivalent of a cation which results in the formation of a salt which is pharmaceutically-acceptable; alkyl having from 1 to 8 carbon atoms or benzyl; and $R^5$ is a hydrogen atom, alkyl having from 1 to 8 carbon atoms or benzyl;

(d)

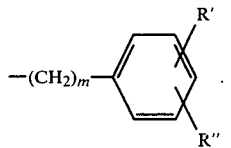

wherein y and y' are as defined above; and j is a whole integer of from 1 to 4, with the proviso that at least one of $R_1$, $R_2$ and $R_3$ is a radical of the formula $$-(CH_2)_m-\underset{R''}{\overset{R'}{\text{Ar}}}$$

31. A composition of claim 30 or 4, provided that when R of the compound is of type (c) then $R^4$ is alkyl or benzyl.

32. A method of claim 3 or 5 provided that when R of the compound is of type (c) then $R^4$ is alkyl or benzyl.

* * * * *